United States Patent
Schlafli et al.

(10) Patent No.: US 8,267,974 B2
(45) Date of Patent: Sep. 18, 2012

(54) CLAMPING DEVICE

(75) Inventors: Christoph Schlafli, Rovio (CH);
Philippe Gicquel, Strasbourg Cedex (FR); Alfred Niederberger, Grenchen (CH)

(73) Assignee: Synthes USA, LLC, West Chester, PA (US)

( * ) Notice: Subject to any disclaimer, the term of this patent is extended or adjusted under 35 U.S.C. 154(b) by 1054 days.

(21) Appl. No.: 11/350,605

(22) Filed: Feb. 8, 2006

(65) Prior Publication Data

US 2006/0195104 A1 Aug. 31, 2006

Related U.S. Application Data

(63) Continuation of application No. PCT/CH03/00538, filed on Aug. 8, 2003.

(51) Int. Cl.
*A61B 17/58* (2006.01)

(52) U.S. Cl. ......... 606/291; 606/304; 606/315; 606/325

(58) Field of Classification Search .................... 606/54, 606/72, 250, 263, 264, 276, 277, 278, 324, 606/300–321, 103, 104; 174/655
See application file for complete search history.

(56) References Cited

U.S. PATENT DOCUMENTS

| | | | |
|---|---|---|---|
| 630,428 A | 8/1899 | Wahlert | |
| 904,341 A * | 11/1908 | Lindstrom | 403/314 |
| 4,068,697 A * | 1/1978 | Schiaffino | 411/270 |
| 4,095,914 A * | 6/1978 | Thomsen | 403/389 |
| 4,250,348 A * | 2/1981 | Kitagawa | 174/655 |
| 4,484,570 A * | 11/1984 | Sutter et al. | 606/282 |
| 4,530,523 A * | 7/1985 | Proni | 285/179 |
| 4,848,953 A * | 7/1989 | Young | 403/290 |
| 5,464,400 A * | 11/1995 | Collins | 604/538 |
| 5,543,582 A * | 8/1996 | Stark et al. | 174/653 |
| 5,601,553 A * | 2/1997 | Trebing et al. | 606/86 B |
| 5,718,706 A * | 2/1998 | Roger | 606/232 |
| 5,746,741 A * | 5/1998 | Kraus et al. | 606/54 |
| 5,797,908 A * | 8/1998 | Meyers et al. | 606/54 |

(Continued)

FOREIGN PATENT DOCUMENTS

FR 782462 6/1935

(Continued)

*Primary Examiner* — Kevin T Truong
*Assistant Examiner* — Christopher Beccia
(74) *Attorney, Agent, or Firm* — Fay Kaplun & Marcin, LLP

(57) ABSTRACT

A device for clamping a fixation element which may allow for repositioning of the fixation element. The device may include a body comprising a front end, a rear end, an outer surface, a through bore extending between the front end and the rear end, a structure enabling deformation of at least a portion of the body, and a thread along at least a portion of the outer surface. The body may be tapered and the through bore may be sized and configured to receive a fixation element. The clamping device may also comprise a receiving member having a tapered bore with an inner thread sized and configured to receive the thread of the body. Insertion of the body into the tapered bore of the receiving member may result in at least a portion of the body being deformed. As the body is inserted into the tapered bore, the dimension of the through bore may decrease so that the body firmly engages the fixation element. Such a construction may allow for the body to be loosened from the tapered bore, the fixation element, body or receiving member to be repositioned, and the body re-tightened into the tapered bore.

19 Claims, 4 Drawing Sheets

U.S. PATENT DOCUMENTS

| | | | | |
|---|---|---|---|---|
| 5,840,078 A | * | 11/1998 | Yerys | 606/151 |
| 5,954,722 A | * | 9/1999 | Bono | 606/281 |
| 6,050,997 A | * | 4/2000 | Mullane | 606/250 |
| 6,126,663 A | * | 10/2000 | Hair | 606/324 |
| 6,235,033 B1 | * | 5/2001 | Brace et al. | 606/288 |
| 6,348,053 B1 | * | 2/2002 | Cachia | 606/327 |
| 6,402,749 B1 | * | 6/2002 | Ashman | 606/278 |
| 6,413,257 B1 | * | 7/2002 | Lin et al. | 606/264 |
| 6,416,515 B1 | * | 7/2002 | Wagner | 606/250 |
| 6,827,722 B1 | * | 12/2004 | Schoenefeld | 606/104 |
| 6,945,972 B2 | * | 9/2005 | Frigg et al. | 606/256 |
| 7,207,995 B1 | * | 4/2007 | Vandewalle | 606/104 |
| 7,276,070 B2 | * | 10/2007 | Muckter | 606/71 |
| 7,311,712 B2 | * | 12/2007 | Dalton | 606/71 |
| 7,396,360 B2 | * | 7/2008 | Lieberman | 606/247 |
| 7,704,257 B2 | * | 4/2010 | Murner | 606/105 |
| 2002/0143341 A1 | | 10/2002 | Biedermann et al. | |
| 2005/0251264 A1 | * | 11/2005 | Katz et al. | 623/21.11 |

FOREIGN PATENT DOCUMENTS

| | | |
|---|---|---|
| GB | 2031731 | 4/1980 |
| JP | 63-158308 | 7/1988 |
| JP | 5-95508 | 12/1993 |
| JP | 2620823 | 4/1997 |
| JP | 2003-512125 | 4/2003 |
| WO | 94/26190 | 11/1994 |
| WO | 01/30251 | 5/2001 |
| WO | 01/67972 | 9/2001 |
| WO | 01/93768 | 12/2001 |
| WO | WO0191660 | 12/2001 |
| WO | 02/00127 | 1/2002 |

* cited by examiner

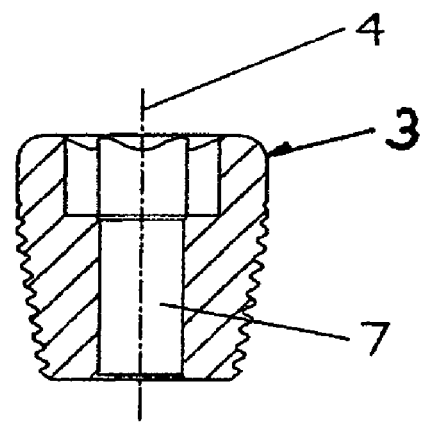
Fig. 2
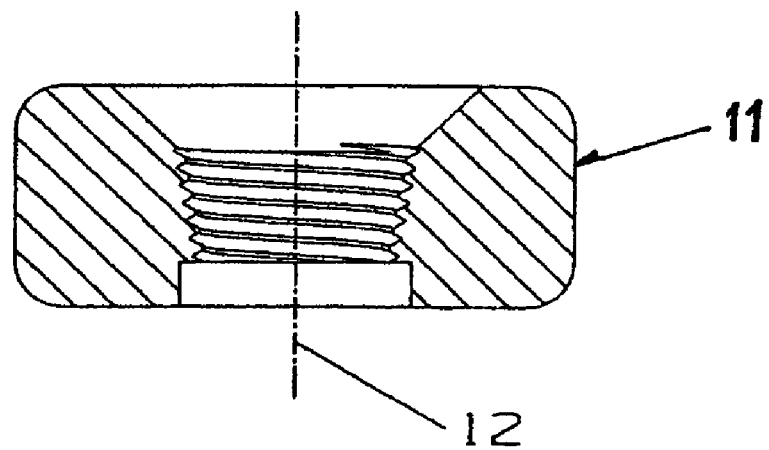

CLAMPING DEVICE

CROSS REFERENCE TO RELATED APPLICATION

The present application is a continuation of International Patent Application PCT/CH2003/000538 filed Aug. 8, 2003, the entire content of which is expressly incorporated herein by reference thereto.

FIELD OF THE INVENTION

The invention relates to a device for holding a fixation element and, in particular, a device which enables the fixation element to be repositioned.

BACKGROUND OF THE INVENTION

In paediatrics, it is desirable to treat fractures of bone in the vicinity of a growth joint while, at the same time, avoiding injury to the growth joint. If the growth joint is injured, the bone will not continue to grow. Therefore, instead of bone screws which are usually used in osteosynthesis, Kirschner wires are used for treating fractures. Kirschner wires have a small diameter and, thus, use of Kirschner wires result in only marginal damage to the growth joint and possibly no injury to the growth joint. The disadvantage of using a Kirschner wire on its own is that the bone fracture cannot be compressed. For this reason, implants have been constructed where a small ball is fastened on the implanted Kirschner wire using a grubscrew. The grubscrew is screwed in at right angle to the Kirschner wire, so that the final position of the Kirschner wire will be secured. This right angle orientation may complicate a surgical technique as well as the manipulation of the Kirschner wire. The grubscrew is situated in the ball and is tightened by means of a tool. The tightening tool is integral with the grubscrew and has a predetermined breaking position. After the fixation of a bone and the Kirschner wire is in position, an operator uses the tool to insert/twist the grubscrew into the ball. When the grubscrew has been tightened into the ball to a certain extent, the application of additional force to the tool may cause the tool to break off from the grubscrew at the predetermined breaking position. Thereafter, the ball is fixed on the Kirschner wire and the ball's positioning can not be reversed or altered (i.e., the Kirschner wire cannot be repositioned).

Accordingly, it is desirable to have a clamping device which may be fixed with respect to a fixation element such as a Kirschner wire and, thereafter, may allow for repositioning of the clamping device and/or fixation element if desired.

SUMMARY OF THE INVENTION

A clamping device may have a body comprising a front end, a rear end, a through bore extending between the front end and the rear end and forming an inner surface, and an outer surface which may extend from the rear end to the front end and may have a tapered shape having a larger width at the rear end. The through bore may be sized and configured to receive a fixation element such as a Kirschner wire. The through bore may have an inner surface which may be straight (ie., forming a cylindrical shape) or may be tapered from one end to the other end (i.e., forming a conical shape). The body may also have a front opening in the front end in communication with the through bore and a rear opening in the rear end in communication with the through bore. Additionally, the body may have at least one slot extending from the outer surface to the inner surface, and a thread along at least a portion of the tapered outer surface. The clamping device may also comprise a receiving member such as, for example, a clamping ring or bone plate.

The body may have a dimension between the outer surface and the bore at the rear end and a dimension between the outer surface and the bore at the front end. The dimension at the rear end may be great than the dimension at the front end. Moreover, the body may be tapered, that is, the body may have a circumference, wherein the circumference of the outer surface of the body at the rear end may be larger than the circumference of the outer surface of the body at the front end. The body may have a structure for enabling deformation of the body, which may be a plurality of slots. The plurality of slots may have a length and the body may have a height from the front end to the rear end, wherein L<0.8 H. The slots may extend from the front end towards the rear end and may be spaced equidistant from each. The body may also have an insertion means positioned within the body (e.g., a recess portion in the rear end for receiving a tool) for inserting the body into a receiving member.

The receiving member may have a bore which may be sized and configured to receive the outer surface of the body. In one embodiment, at least a portion of the bore may be tapered or conically shaped. In an embodiment where the receiving member is a bone plate, the bone plate may have a plurality of holes, wherein at least one of the holes may be tapered and may be sized and configured to receive the body. The tapered bore or hole of the receiving member may have an internal thread which is sized and configured to engage the thread of the body. In some embodiments, the thread of the body may have two starts for improved threading of the body into the tapered bore. The body may be inserted into the tapered bore or hole so that at least a portion of the body (e.g., the front end of the body) may deform. With a fixation element positioned in the through bore, such deformation may results in the body being fixed with respect to the fixation element. In order to enhance the grip of the body on the fixation element, the inner surface of the body may have a textured surface, a roughened surface, a knurled surface or a macroscopic structure.

A method of clamping a fixation element (e.g., Kirschner wire) in a patient may include providing a clamping device. The clamping device may have a body, a receiving member and a recess portion within the body (e.g., in the rear end of the body) for receiving a tool for inserting the body into the receiving member. The body may comprise a front end, a rear end, a through bore, a plurality of slots, a taper extending from the rear end to the front end and a thread along at least a portion of the taper. The through bore may have a dimension sized and configured to receive a fixation element and may extend between the front end and the rear end. The receiving member may have a tapered bore which has an inner thread.

The method may also comprise placing the receiving member against tissue of the patient, inserting the front end of the body into the tapered bore of the receiving member, inserting the fixation element through the through bore and into tissue, and, thereafter, tightening the body in the tapered bore to fixedly clamp the fixation element to the receiving member.

The method may further comprise inserting the body into the tapered bore of the receiving member, deforming at least a portion of the body as the thread of the body is screwed into the inner thread of the tapered bore of the receiving member, and reducing the dimension of the through bore so that a fixation element positioned into the through bore is fixed with respect to the body. Upon insertion into the tapered bore, the body may be radially deformed. The construction of the clamping device may enable the clamping device and/or fixation element to be reposition. In particular, the body may be unscrewed/loosened so that the body may be at least partially out of the tapered bore of the receiving member. Thereafter, the clamping device and/or fixation element may be repositioned. The body may then be screwed/inserted back into the tapered bore of the receiving member so that the clamping device may be fixed with respect to the fixation element.

BRIEF DESCRIPTION OF THE DRAWINGS

The invention and further developments of the invention are explained in even greater detail in the following exemplary drawings. The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 2 is a cross sectional view of the device of FIG. 1;

DETAILED DESCRIPTION

Figure 1:
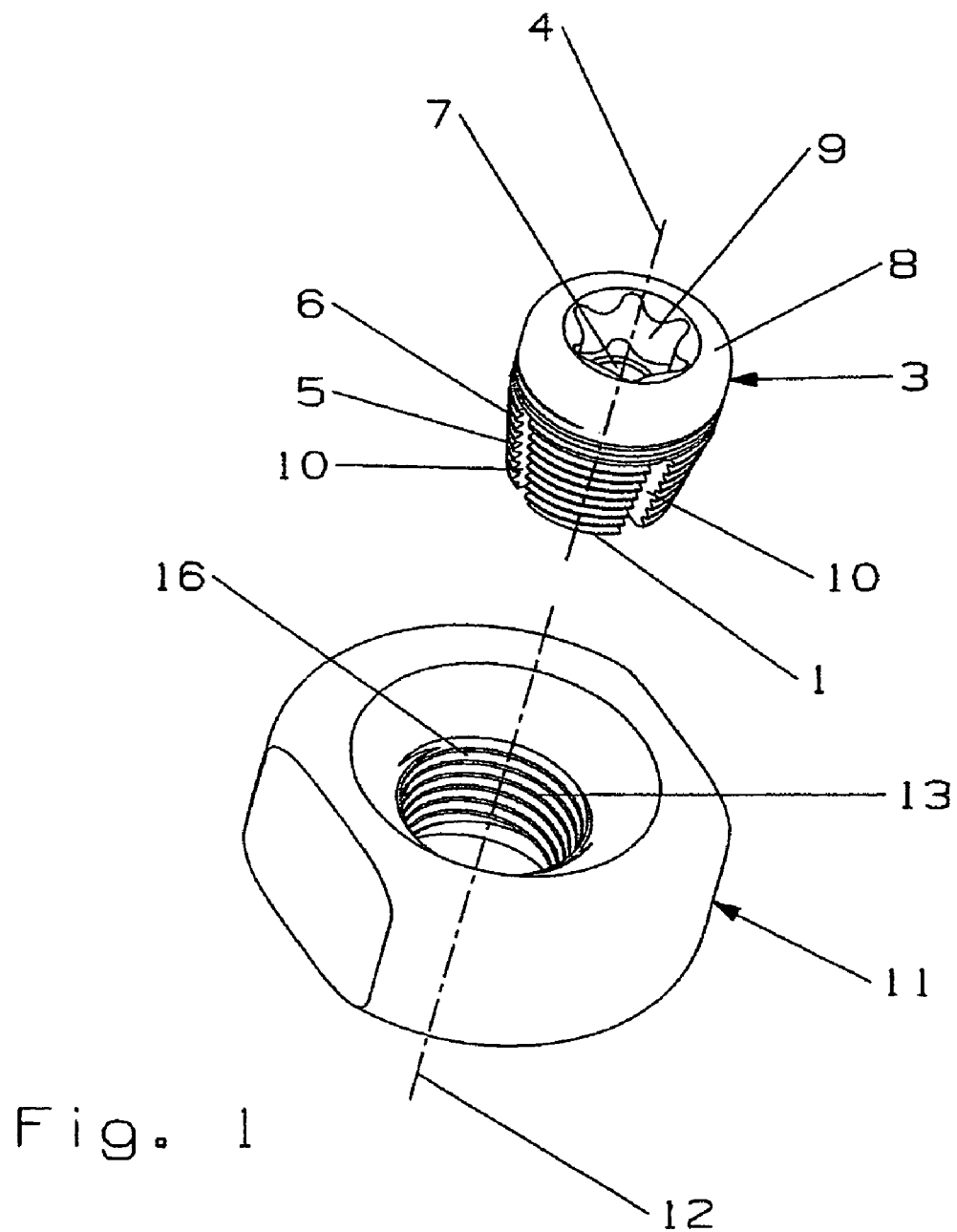
FIG. 1 is a perspective view of one embodiment of the clamping device incorporating an exemplary receiving member.

As illustrated in FIGS. 1 and 2, the clamping device may include a body or screw 3 and a receiving member (e.g., clamping ring 11). The screw 3 may have a partly truncated conical shape and may have a through bore 7. It should, however, be understood that those of ordinary skill in the art will recognize many modifications and substitutions which may be made to various elements of the present invention. The clamping device of the present invention may be used for paediatric application, but may also be used in adults at well. The clamping device may be used to connect a fixation element to any bone in the body (e.g., proximal end of the humerus).

The screw 3 may have a front end 1, a rear end 8, an outer surface, an inner surface and a height from the front end 1 to the rear end 8 of between about 3 mm and about 7 mm. Moreover, the outer surface of the screw 3 may taper from a rear end 8 to a front end 1 such that the taper is between about 15° and about 25° and such that the dimension (or circumference) at the rear end 8 may be greater than the dimension (or circumference) at the front end 1. The screw 3 may also have a jacket surface 5 including a taper thread 6 along at least a portion of the jacket surface 5 and a taper axis 4. The jacket surface 5 may have a thickness (i.e., between the outer surface of the screw 3 and the through bore 7) of about 4.0 mm at the rear end 8 and a thickness of about 0.8 mm at the front end 1. The through bore 7 of the screw 3 may be coaxial with the taper axis 4 and may have a diameter of between about 1.0 mm and about 3.0 mm. The through bore 7 may be straight and may be cylindrical in shape. Alternatively, the through bore 7 may be tapered from one end to the other end (i.e., the through bore 7 may be conical in shape).

The screw 3 may have a plurality of longitudinal slots 10 which may have a length L and which may extend substantially parallel to the taper axis 4. The length L may be measure from the front end 1 of the screw 3 to the rear end 8 and may be between about 2.5 mm and about 4.5 mm. In one embodiment, the length L of the longitudinal slots 10 may be less than the overall height H of the screw 3 such that L<0.8 H. The slots 10 may have a width of between about 0.3 mm and about 1.2 mm. The slots 10 may enable the screw 3 to radially flex along at least a portion of the screw 3. Moreover, the longitudinal slots 10 may be open at a front end 1 of the screw 3 and may extend from the jacket surface 5 into the through bore 7. When a cross-section (not shown) of the screw 3 is viewed from a plane which is perpendicular to the taper axis 4, the longitudinal slots 10 may be symmetrically distributed about the screw 3 (e.g., longitudinal slots 10 may be positioned every 90°). In one embodiment, the front end 1 of the screw 3 may have three or more longitudinal slots 10, which may be equidistant from each other.

The rear end 8 of the screw 3 may have means 9 by which the screw 3 may be engaged by a device used to insert/screw the screw 3 into or remove the screw 3 from a receiving member (e.g., clamping ring 11 or bone plate 14). In one embodiment, the means 9 may be a recess portion which may penetrate the rear end 8 of the screw 3 (i.e., a recess portion which may be positioned within the rear end 8). The means 9 may be coaxial with the taper axis 4. As shown in FIGS. 1 and 2, the means 9 may be in the shape of a hexagon. Those skilled in the art will appreciate that the means 9 may be any other shape so long a the means 9 is sized and configured to receive a device for inserting the screw 3 in a receiving member (e.g., clamping ring 11 or bone plate 14). In another embodiment, the jacket surface 5 may be polygonal shape at the rear end 8. A device may be positioned over the rear end 8 of the screw 3 and may engage the polygonal shaped portion to move the screw 3 in and/or out of the receiving member.

As illustrated in FIG. 1, the clamping ring 11 may have a central axis 12 and a tapered bore 13. In one embodiment, the clamping ring 11 may be cylindrical in shape, however, the clamping ring 11 may be any other shape (e.g., polygon). The tapered bore 13 of the clamping ring 11 may have an internal thread 16 which may be sized and configured to receive the thread 6 of the screw 3. Insertion of the screw 3 into the tapered bore 13 may cause radial compression of at least a portion of the screw 3 (e.g., the region about the front end 1 of the screw 3).

Figure 4:
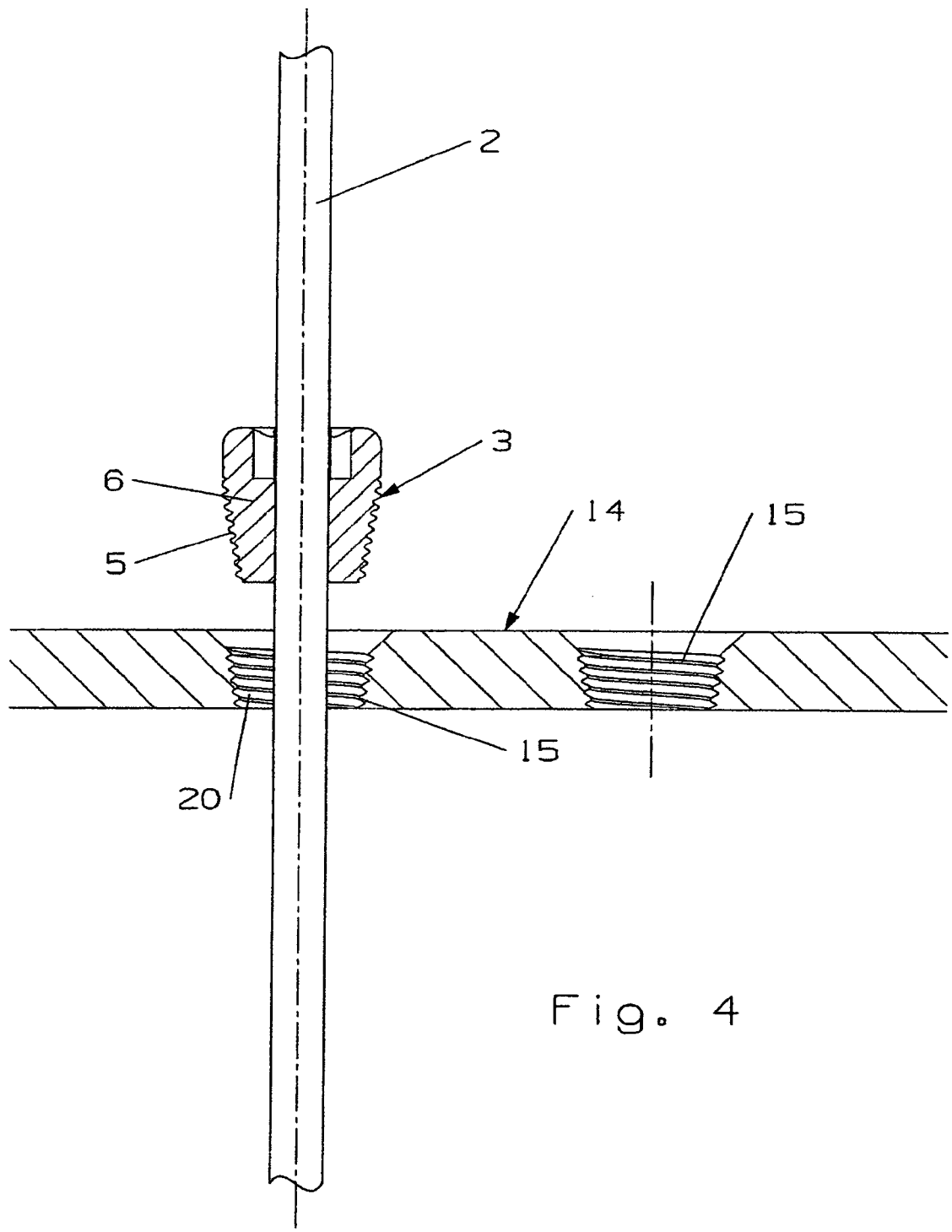
FIG. 4 is a cross sectional view of an alternative embodiment of the clamping device incorporating another exemplary receiving member.

Those skilled in the art will appreciate that the screw 3 may be used with any other type of receiving member such as the bone plate of FIG. 4. The bone plate 14 may have a plurality of holes at least one of which may be tapered hole 15 with a tapered internal thread 20. The tapered internal thread 20 may match the thread 6 on the jacket surface 5 of the screw 3. A screw 3 may be screwed into each tapered hole 15 of the plate 14. Similar to above, when the screw 3 is inserted/screwed into a hole 15 of the plate 14, the screw 3 may radially compress along a radially flexible segment of the screw 3—the portion of the screw 3 along at least a portion of the length L. In this way, a Kirschner wire may be used in place of or in addition to a bone screw (not shown) to fasten the bone plate 14 to a bone.

Figure 3:
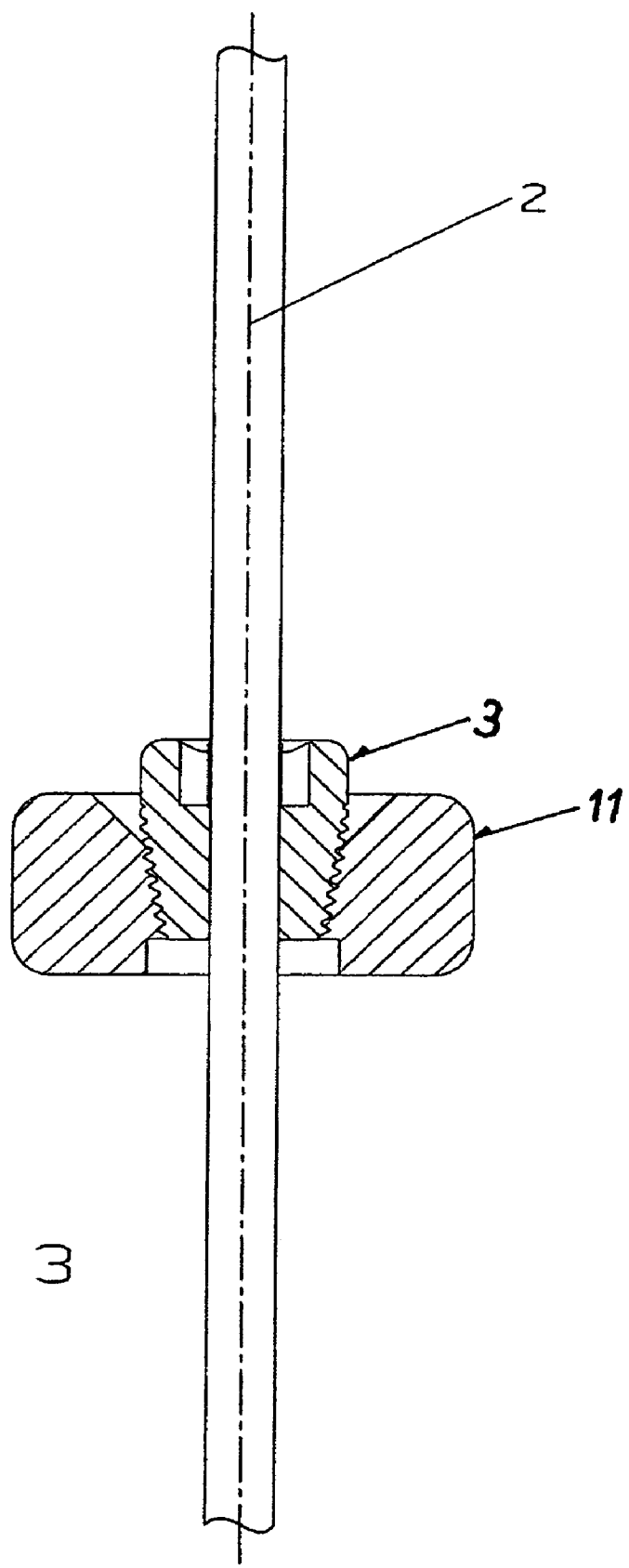
FIG. 3 is a cross sectional view of the device of FIG. 1 assembled with a fixation element.

In use, as shown in FIGS. 3 and 4, a fixation element such as a Kirschner wire 2 may be inserted into the through bore 7 of the screw 3. The screw 3 may then be inserted/screwed into the clamping ring 11 or plate 14. In one embodiment, the Kirschner wire 2 may be inserted into the screw 3 after the screw 3 is partially inserted/screwed into the receiving member. Thereafter, the screw 3 may be further tightened into the receiving member to fixedly connect the fixation element to the receiving member. Alternatively, the screw 3 and Kirschner wire 2 may be assembled and inserted together into the receiving member. In another embodiment, the Kirschner wire 2 may be inserted through a bore/hole of the receiving member, the screw 3 may then be inserted over the Kirschner wire 2 and tightened into the bore/hole of the receiving member to connect the Kirschner wire 2 and the receiving member. In one embodiment, the taper thread 6 of the screw 3 may have two starts, which may have a pitch of, for example, between about 0.6 mm and about 1.1 mm and, more preferably, about 0.8 mm. A thread 6 having two starts may facilitate insertion of the screw 3 into the bore 13, because the thread 6 may engage the tapered bore 13 or hole 15 and, in particular, the internal thread 16, 20 more quickly than a screw with a single-start thread. Prior to insertion of the screw 3 into the ring 11 or plate 14, the clearance between fixation element and the through bore 7 may be between about 0 mm and about 0.1 mm. As the screw 3 moves into the tapered bore 13 or tapered hole 15 of the receiving member, at least a portion of the screw 3 may be radially compressed. In particular, the radially flexible portion of the screw 3—the portion of the screw 3 along at least a portion of the length L—may deform as the screw 3 is inserted into the tapered bore 13 or tapered hole 15. Consequently, the dimension of the through bore 7 (at a right angle to the taper axis 4) may be reduced. Such deformation results from the truncated cone shape of the screw 3 being inserted into the matching taper-shaped bore 13 or hole 15. In this way, a fixation element may be fixed with respect to the screw 3 and receiving member. Moreover, in order to enhance the grip or obtain a better clamping effect of the screw 3 on the fixation element, the through bore 7 may have an inner wall which may be textured, roughened or knurled or may have a macroscopic structure.

The configuration of the clamping device enables the clamping device to be attached at any location along the length/axis of the Kirschner wire 2. In addition, the configuration of the clamping device enables a user to re-adjust the position of the fixation element and/or the clamping device until the user is satisfied with the position. For example, the screw 3 may be at least partially unscrewing or removed from the tapered bore 13 or hole 15 of the receiving member, the screw 3, receiving member and/or fixation element may then be repositioned relative to each other. Thereafter, the screw may be screwed/inserted back into the tapered bore 13 or hole 15 of the receiving member thereby fixing the position of the screw 3, the receiving member and the fixation element.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A clamping device, comprising:
    a body comprising a front end, a rear end, a through bore extending between the front end and the rear end forming an inner surface, the through bore sized and configured to receive a fixation element, an outer surface extending from the rear end to the front end, the outer surface having a tapered shape having a larger width at the rear end, at least one slot extending from the outer surface to the inner surface, a thread along at least a portion of the tapered outer surface, and a recess portion positioned in the rear end of the body for inserting the body into a receiving member, wherein the recess portion is coaxial with the through bore and does not communicate with the outer surface, and wherein the thread has two starts.

2. The device of claim 1, wherein the receiving member is selected from at least one of the group consisting of a clamping ring and a bone plate.

3. The device of claim 2, wherein the receiving member comprises a tapered bore which is sized and configured to receive the body, the tapered bore having an internal thread.

4. The device of claim 3, wherein the front end of the body deforms upon insertion into the tapered bore.

5. The device of claim 1, wherein the inner surface is selected from at least one of the group consisting of a textured surface, a roughened surface and a knurled surface.

6. The device of claim 1, wherein the at least one slot has a length which is between about 2.5 mm and about 4.5 mm.

7. The device of claim 1, wherein the body has a height extending from the front end to the rear end and the at least one slot has a length, wherein $L<0.8\,H$.

8. The device of claim 1, wherein the body has a plurality of slots, wherein the slots are spaced equidistant from each other.

9. The device of claim 1, wherein the at least one slot extends from the front end towards the rear end.

10. The device of claim 1, wherein the fixation element is a Kirschner wire.

11. A clamping device, comprising:
    a body comprising a circumference, a front end, a rear end, an outer surface, a through bore extending between the front end and the rear end and forming an inner surface, the through bore sized and configured to receive a fixation element, a deformation enabling structure, a thread along at least a portion of the outer surface, a front opening in the front end in communication with the through bore and a rear opening in the rear end in communication with the through bore, wherein the circumference of the outer surface of the body at the rear end is larger than the circumference of the outer surface of the body at the front end;
    a receiving member having a bore sized and configured to receive the outer surface of the body, the bore having at least a portion that is both conically shaped and has an inner thread; and a recess portion within the rear end of the body for receiving a tool for inserting the body into the receiving member, wherein the recess portion is coaxial with the through bore and does not communicate with the outer surface, and wherein the thread has two starts.

12. The device of claim 11, wherein the deformation enabling structure comprises a plurality of slots extending from the front end towards the rear end and extending from the outer surface to the inner surface.

13. The device of claim 11, wherein the through bore is tapered.

14. The device of claim 11, wherein the receiving member is selected from at least one of the group consisting of a clamping ring and a bone plate.

15. The device of claim 11, wherein the through bore has an inner wall which has at least one of the group consisting of a textured surface, a roughened surface and a knurled surface.

16. A method for clamping a Kirschner wire in a patient, comprising:
providing a clamping device comprising:
a body comprising a front end, a rear end,
a through bore having a dimension and extending between the front end and the rear end, a plurality of slots, an outer surface extending from the rear end to the front end, at least a portion of the outer surface being tapered so that the outer surface is larger at the rear end, and a thread along at least a portion of the tapered outer surface;
a receiving member having a tapered bore, wherein the tapered bore has an inner thread; and
a recess portion within the rear end of the body for receiving a tool for inserting the body into the receiving member;
inserting the Kirschner wire into the through bore; and
inserting at least a portion of the body into the tapered bore of the receiving member, whereby the body is deformed to reduce the dimension of the through bore so that the Kirschner wire positioned into the through bore is fixed with respect to the body, wherein the recess portion is coaxial with the through bore and does not communicate with the outer surface, and wherein the thread has two starts.

17. The method of claim 16, further comprising: placing the receiving member against tissue of the patient; inserting the front end of the body into the tapered bore of the receiving member; inserting the Kirschner wire through the through bore and into tissue; and thereafter tightening the body in the tapered bore to fixedly clamp the Kirschner wire to the receiving member.

18. The method of claim 16, wherein the deforming step is radial deformation.

19. The method of claim 16 further comprising: unscrewing the body at least partially out of the tapered bore of the receiving member; repositioning the body on the fixation element; and screwing the body back into the tapered bore of the receiving member.

* * * * *